US006429968B1

(12) United States Patent
Carver (10) Patent No.: US 6,429,968 B1
(45) Date of Patent: Aug. 6, 2002

(54) APPARATUS FOR PHOTOLUMINESCENCE MICROSCOPY AND SPECTROSCOPY

(75) Inventor: Gary E. Carver, Raritan Township, Hunterdon County, NJ (US)

(73) Assignee: Agere Systems Guardian Corp, Berkeley Heights, NJ (US)

( * ) Notice: Subject to any disclaimer, the term of this patent is extended or adjusted under 35 U.S.C. 154(b) by 0 days.

(21) Appl. No.: 09/522,098

(22) Filed: Mar. 9, 2000

(51) Int. Cl.[7] ............................. G02B 21/00; F21V 9/16; G01J 3/28
(52) U.S. Cl. ..................... 359/385; 359/368; 250/458.1; 356/326
(58) Field of Search ................................. 356/451, 300, 356/318, 326; 359/331, 385, 368; 250/458.1, 459.1, 341.4, 341.2

(56) References Cited

U.S. PATENT DOCUMENTS

| | | |
|---|---|---|
| 4,652,757 A | 3/1987 | Carver |
| 5,007,741 A | 4/1991 | Carver et al. |
| 5,161,053 A | 11/1992 | Dabbs |
| 5,192,980 A | 3/1993 | Dixon et al. |
| 5,381,224 A | 1/1995 | Dixon et al. |
| 5,386,112 A | 1/1995 | Dixon |
| 5,532,873 A | 7/1996 | Dixon |
| 5,737,121 A | 4/1998 | Dixon |
| 5,760,951 A | 6/1998 | Dixon et al. |
| 6,040,907 A * | 3/2000 | Steiner et al. ............... 356/311 |
| 6,194,711 B1 * | 2/2001 | Tomita ........................ 250/216 |

OTHER PUBLICATIONS

Carver, Scanned Photoluminescence With High Spatial Resolution in Semi–Insulating GaAs And InP: Aspects of Surface Passivation and Photodegradation, Semicond. Sci. Tech. 7(1992) A53–A58.

Xie et al., "Absorption and Luminescence Studies of Free–Standing Porous Silicon Films," Physical Review B, vol. 49, No. 8, Feb. 15, 1994, pp. 5386–5397.

Carver et al., "Non–Destructive Optical Techniques For Characterizing Semiconductor Materials and Devices," AT&T Technical Journal, Mar./Apr. 1994, pp. 66–76.

Ribes et al., "Photoluminescence Imaging of Porous Silicon Using A Confocal Scanning Laser Macroscope/Microscope," Appl. Phys. Lett. 68 (18) May 1, 1995, pp. 2321–323.

Carver et al., "Wafer Level Testing For Semiconductor Laser Manufacture Via Spatially Resolved Photoluminescence," IEEE Journal of Selected Topics In Quantum Electronics, vol. 1, No. 4, Dec. 1995, pp. 980–986.

Carver et al., "Optical Testing Methods For Organic Electroluminescent Displays," Synthetic Metals 91 (1997) 117–119.

* cited by examiner

Primary Examiner—Frank G. Font
Assistant Examiner—Roy M. Punnoose
(74) Attorney, Agent, or Firm—Law Offices of John. De La Rosa

(57) ABSTRACT

In accordance with the teachings of the present invention, it has been discovered that an optical analysis that is uniquely based on geometrical rather than diffraction considerations, for the purposes of controlling the size of the region from which the photoluminescence is collected, provides an optical system capable of performing photoluminescence microscopy and/or spectroscopy without the disadvantages of the prior art. It is based, in part, on the use of an optical fiber(s) as a field stop within the detection arm(s) of the optical system for coupling the photoluminescence into an optical spectrum analyzer (OSA) and/or photodetector, wherein the diameter and the numerical aperture of the optical fiber are judiciously chosen to limit the field of view, or the region from which the photoluminescence is collected.

42 Claims, 8 Drawing Sheets

APPARATUS FOR PHOTOLUMINESCENCE MICROSCOPY AND SPECTROSCOPY

TECHNICAL FIELD

The present invention relates to optical microscopy and, more particularly, to photoluminescence microscopy and spectroscopy used to map material quality in semiconductor wafers and devices.

BACKGROUND OF THE INVENTION

In the information age, communications technology depends on the efficient manufacture of photonic and electronic devices. Optical testing promotes manufacturing efficiency by controlling the quality of incoming materials, providing rapid feedback for process improvements, and analyzing why a product has failed. New, non-destructive optical techniques are being used to measure key properties of semiconductor materials and devices. Optical mapping reveals defective regions in various types of wafers, as well as in optoelectronic devices, such as lasers, modulators and detectors, used in lightwave communications systems.

Spatially resolved photoluminescence is particularly valuable for measuring and characterizing the radiative uniformity of optoelectronic materials, wafers, epitaxial layers and devices. In spatially resolved photoluminescence, the semiconductor wafer or device is irradiated with a beam of highly focused monochromatic light having energy greater than the bandgap energy of the semiconductor. As this so-called "pumping" beam is scanned over an area of the wafer, broadband photoluminescence from the surface is detected, with changes in the intensity of the photoluminescence indicative of defects, such as dislocations. Moreover, displaying the intensity of the photoluminescence on a video monitor creates a spatially resolved photoluminescence image.

Figure 1:
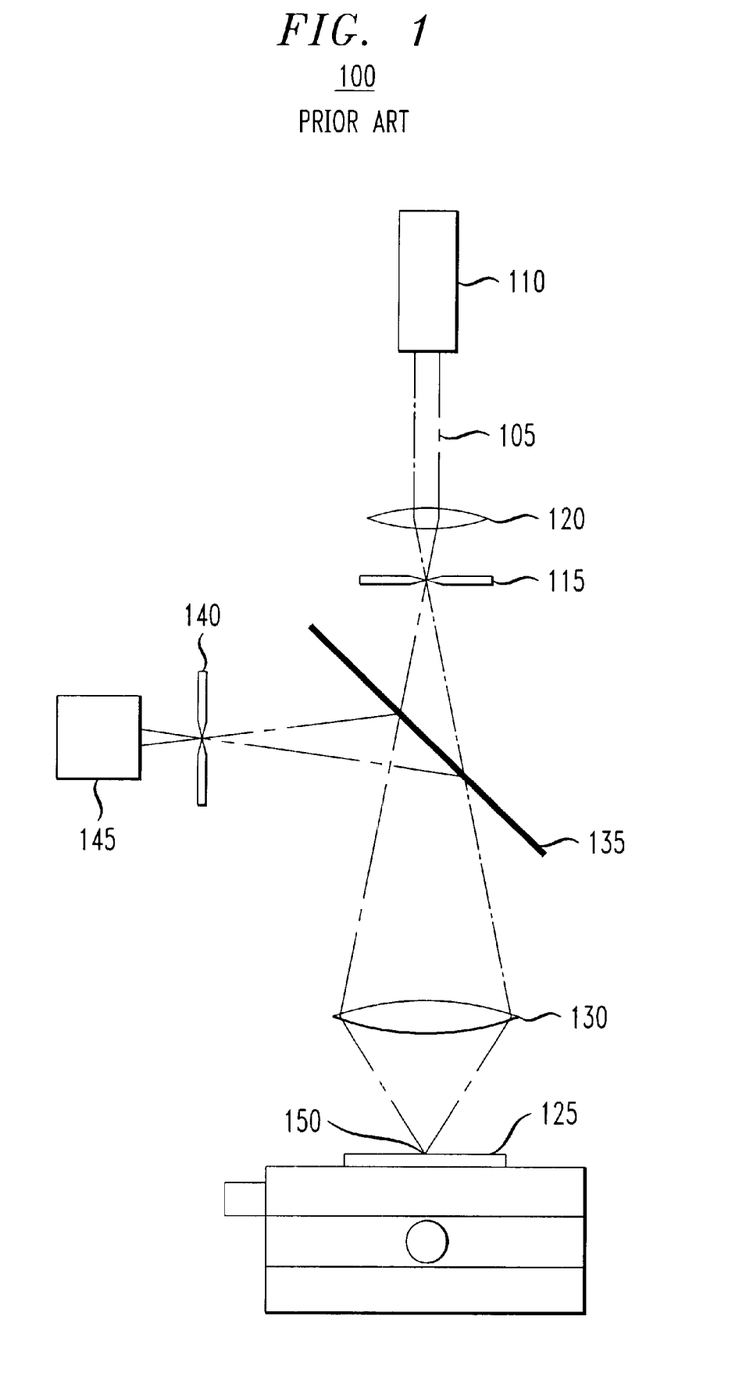
FIG. 1 is a simplified view of a confocal laser microscope of the prior art.

In the prior art, confocal laser microscopes have been adapted to detect photoluminescence with high spatial resolution. For example, shown in FIG. 1, is a confocal scanning laser microscope 100 which utilizes its confocal properties to separate the photoluminescence originating from different points on the semiconductor. In this latter configuration, light 105 from laser 110 is focused through pinhole 115 by lens 120, and then into a diffraction-limited spot on the surface of semiconductor 125 by objective lens 130. Photoluminescence from the semiconductor surface, and within this diffraction limited spot, is directed by dichroic beamsplitter 135, and focused by objective lens 130 through pinhole 140 onto detector 145. Dichroic beamsplitter 135 transmits light from laser 110, but only directs longer wavelength photoluminescence onto detector 145.

Photoluminescence substantially only originating from focused spot 150 passes through pinhole 140. Light from any other point on the semiconductor is blocked by the edges of the pinhole inasmuch as focused spot 150 is confocal with pinholes 115 and 140, giving this configuration the ability to obtain highly spatially resolved photoluminescence images.

Spectrally resolved photoluminescence, on the other hand, is generally used to measure the compositional characteristics of the semiconductor material, such as bandgap energy, donor and acceptor energy levels, phonon energy, and the like. In spectrally resolved photoluminescence, highly monochromatic light is used to excite an area of the semiconductor, with the resulting photoluminescence directed into a monochromator which resolves the spectral components of the photoluminescence. For example, certain photoluminescence systems sold by Waterloo Scientific Inc., focus the photoluminescence onto the entrance slit of a grating monochromator.

Figure 2:
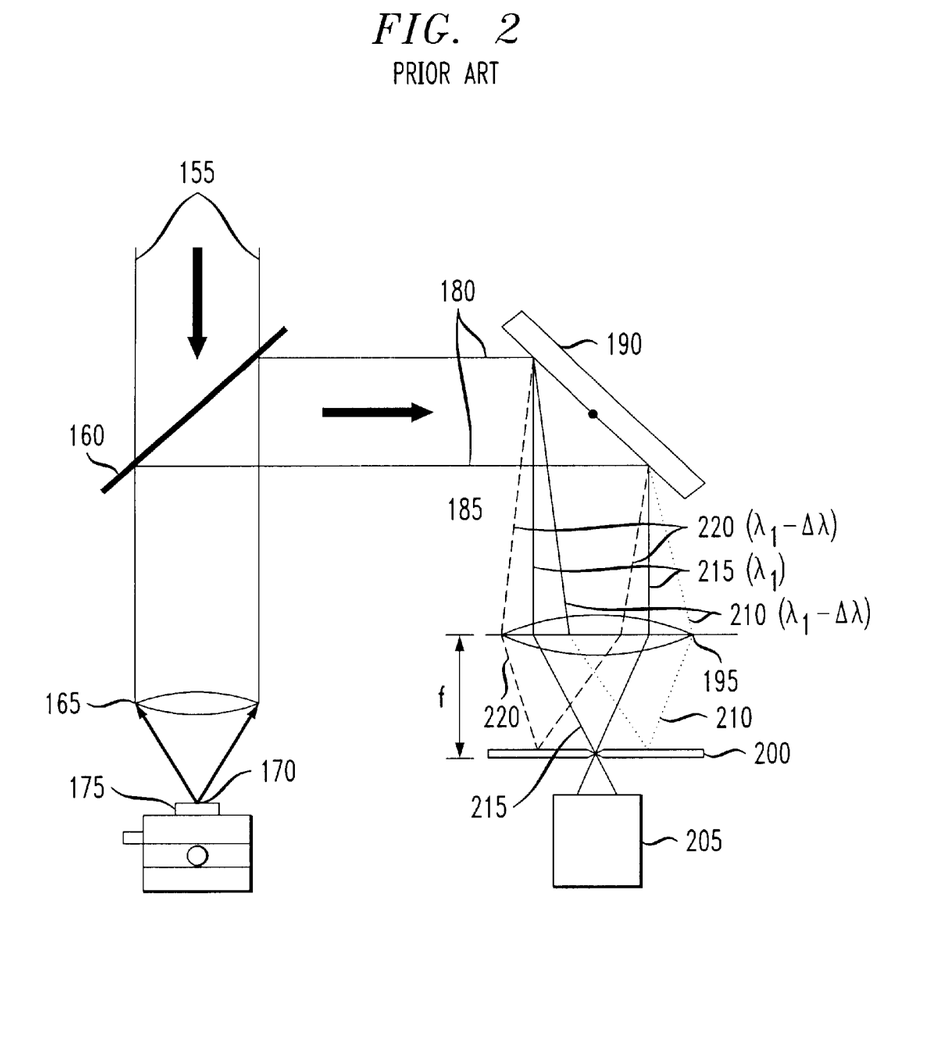
FIG. 2 is a simplified view of a confocal laser microscope of the prior art adapted for performing both microscopy and spectroscopy.

Unfortunately, such prior art photoluminescence systems do not readily allow an operator to make both spatially as well as spectrally resolved photoluminescence measurements, particularly with spatial resolutions in the micron ($\mu$m) region. Additionally, such photoluminescence systems only pass a fraction of the collected photoluminescence to the detector. However, a spectrally resolved photoluminescence mapping of semiconductor wafers with good spatial resolution and collection efficiency has been recently disclosed by Dixon et al. in U.S. Pat. No. 5,192,980, which is incorporated herein by reference. Referring to FIG. 2, Dixon et al. integrates a monochromator or spectrometer into the detection arm of a confocal microscope adapted to obtain highly spatially resolved photoluminescence spectra of the semiconductor. More specifically, a parallel beam 155 of laser light passes through a beamsplitter 160 to enter objective lens 165 which focuses the beam to a diffraction limited focal spot 170 on the surface of a semiconductor specimen 175. On-axis photoluminescence 180 from the specimen is collected by objective lens 165, and is then partially reflected by beamsplitter 160 into a detection arm 185 of the microscope. On-axis photoluminescence 180 strikes diffraction grating 190 which diffracts the light toward lens 195, placed a focal length, f, in front of a pinhole 200. That is, pinhole 200 is confocal with focal spot 170 at the focal point of lens 165.

Inasmuch as diffraction grating 190 separates incoming light 180 into its spectral components along a longitudinal axis, only photoluminescence of a narrow wavelength band passes through pinhole 200, and reaches detector 205. Shown in FIG. 2 are exemplary spectral components 210 ($\lambda_{-1}+\Delta\lambda$), 215 ($\lambda_{-1}$), 220 ($\lambda_{-1}-\Delta\lambda$), with only spectral component 215 (centered at $\lambda_{-1}$) passing through pinhole 200. Light centered at any other wavelength emitted from focal spot 170 hits the area surrounding pinhole 200, and is not detected.

Unfortunately, the photoluminescence system of Dixon et al., and similar confocal based photoluminescence systems, are generally ill-suited for semiconductor specimens exhibiting substantial lateral carrier diffusion.

SUMMARY OF THE INVENTION

In accordance with the teachings of the present invention, it has been discovered that when the lateral carrier diffusion area exceeds the diffraction limit spot of the illuminating beam, an optical analysis that includes the extended size of the carrier diffusion area provides a technique for more properly controlling the size of the PL collection region or the axial photoluminescence resolution. On the above basis, the optical system is uniquely characterized in that the optical fiber(s) within the detection arm(s) of the optical system functions as the effective field stop for off-axis photoluminescence. As the field stop, the optical fiber(s) limits the size or field of view of the photoluminescence corresponding to a PL collection region of desired radius. Importantly, it does so, by limiting the cone of light accepted from the off-axis photoluminescence vis-a-via its core size and numerical aperture.

Thus, the underlying rational in controlling the spatial resolution for an extended region of photoluminescence is to judiciously choose the core radius, and the numerical aperture of the optical fiber(s) so as to control the conical bundle of rays from points on the periphery of the desired photoluminescence region so as to reach and enter the optical fiber(s).

In a preferred embodiment, light from a laser is focused into a diffraction limited spot and scanned on the surface of a semiconductor specimen in a predetermined pattern. The photoluminescence from the semiconductor surface is then directed and focused onto the optical fiber, which by judiciously choosing its core diameter and numerical aperture, functions as the field stop to limit the photoluminescence collection region to a desired radius. Photoluminescence spectroscopy and/or microscopy is performed by coupling the collected photoluminescence within the optical fiber into an optical spectrum analyzer and/or photodetector, using optical coupling means or optical switches.

In one embodiment, since collected photoluminescence incident outside the core of the optical fiber is not detected, limiting the PL collection region to a desired radius requires that the photoluminescence from any point outside the desired radius has its conjugate image also outside the core radius. To do so, requires setting the ray height of the principal ray of the collected photoluminescence from the periphery of the PL collection region to the core radius of the optical fiber. This constraint requires, however, that some of the collected photoluminescence falls within the acceptance cone or numerical aperture of the optical fiber.

Alternatively, the numerical aperture of the optical fiber can be tailored to control the radius of the PL collection region, instead of the core radius. At some off-axis point of the PL collection region, no light will be accepted by the optical fiber since all rays incident on the core exceed the maximum external slope of the ray that can be totally internal reflected within the fiber. In this later case, the minimum ray angle of the off-axis marginal rays from the periphery of the desired PL collection region should just match the numerical aperture $NA_{fiber}$ of the optical fiber. The photoluminescence from the periphery of the desired collection region, however, should reach a conjugate image point inside the core.

One advantage of the present invention is that it can readily utilize fiber technology to enhance performance. For example, optical amplifiers can be built into the optical fiber(s) to increase the signal level of the collected photoluminescence, without the need to increase the power level of the light used to excite the semiconductor specimen. Additionally, a spectrometer may be fabricated within the optical fiber, allowing more efficient light path for spectrally resolving the photoluminescence, as well as resulting in a more compact system.

BRIEF DESCRIPTION OF THE DRAWINGS

The features and advantages of the present invention will become more readily apparent from the following detailed description of the invention in which like elements are labeled similarly and in which.

DETAILED DESCRIPTION

Figure 3:
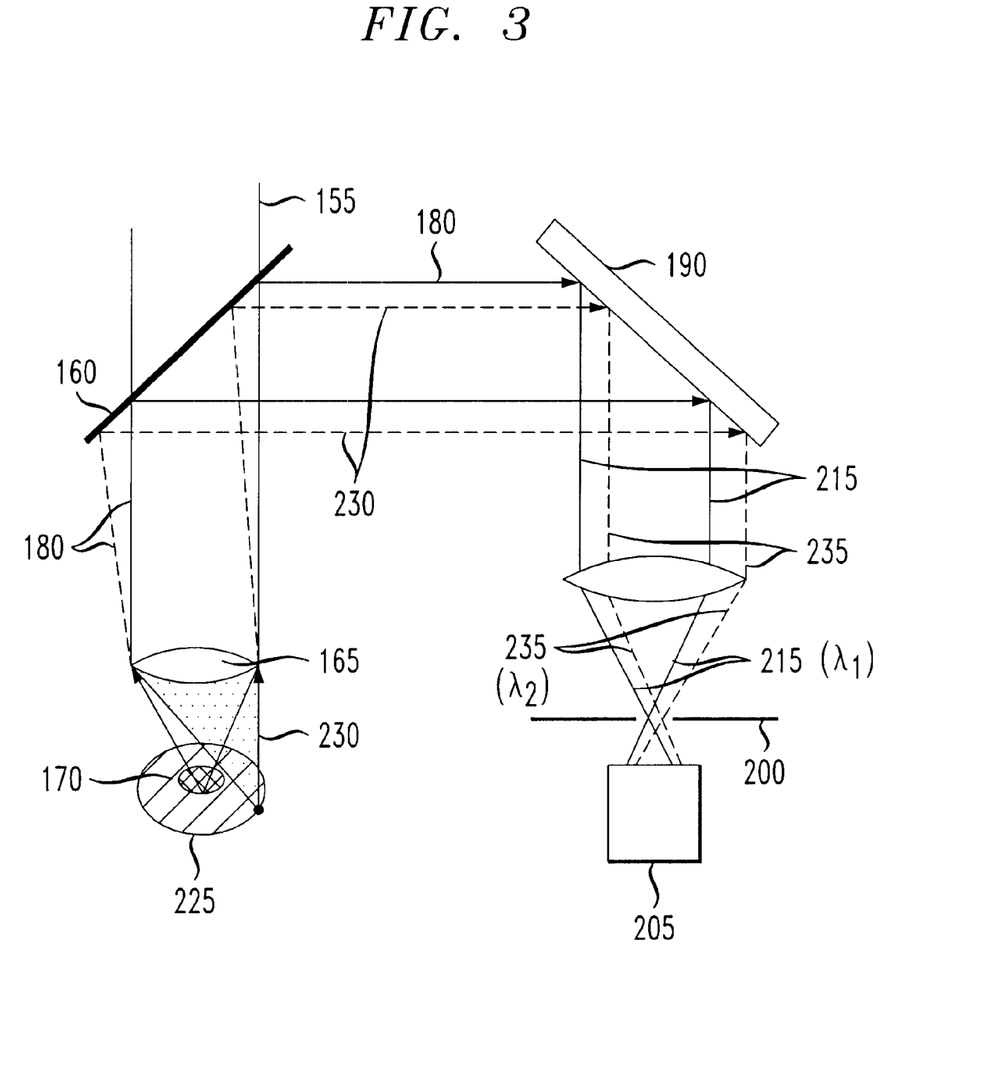
FIG. 3 is an illustration depicting a diffraction limited focal spot and carrier diffusion area of the confocal laser microscope of FIG. 2.

Although effective for reflective microscopy, confocal microscope systems, similar to those disclosed in Dixon et al., are generally ill-suited for performing both spectroscopy and microscopy in semiconductor specimens exhibiting substantial lateral carrier diffusion. More specifically, those designs allow on-axis photoluminescence of one wavelength to be contaminated with off-axis photoluminescence of another wavelength, particularly if the semiconductor specimen exhibits a lateral carrier diffusion substantially larger than the diffraction pattern or so-called "Airy disc" of the "pumping" beam. Referring to FIG. 3, although parallel beam 155 of Dixon et al. is only focused into a small focal spot 170, lateral carrier diffusion may, and typically does, cause photoluminescence to occur outside focal spot 170, shown herein as diffusion carrier area 225. Off-axis photoluminescence 230, shown herein stippled, is similarly collected by lens 165, and likewise diffracted and separated into its spectral components. Unfortunately, a spectral component 235 of the off-axis photoluminescence, but at another wavelength ($\lambda_2$), can be diffracted, and likewise be focused onto the same location as pinhole 200, thereby reaching detector 205 and contaminating the on-axis photoluminescence ($\lambda_1$) from focal spot 170. As such, for semiconductor specimens exhibiting significant lateral carrier diffusion, photoluminescence of another wavelength from points outside the focal spot is not necessarily blocked by the edges of the pinhole, even though the microscope is confocal.

As described herein below, the inventive optical system of the present invention advantageously performs photoluminescence microscopy and/or spectroscopy without the disadvantages of the prior art, particularly being well suited for semiconductor specimens exhibiting lateral carrier diffusion that extends substantially beyond the focal spot of the illuminating beam or so-called "pumping beam." It is based, in part, on the use of an optical fiber(s) as a field stop within the detection arm(s) of the optical system for coupling the photoluminescence into an optical spectrum analyzer (OSA) and/or photodetector, wherein the diameter and the numerical aperture of the optical fiber(s) are judiciously chosen to limit the field of view, or the region from which the photoluminescence is collected (hereinafter the "PL collection region").

Optoelectronic devices that functionally integrate lasers, modulators, semiconductor amplifiers, detectors, wavelength tuners, and the like, particularly benefit from the present invention. In such devices, the raster scan is positioned over critical features of the device structure, where it is critical to only collect the photoluminescence over a controlled spatial region of the device, ranging from about 1–10 $\mu$m, such as the absorbing region of the detector or the active mesa of the laser.

Unlike prior art systems, the present invention is based on an optical analysis that is uniquely based on geometrical rather than diffraction considerations, for the purposes of controlling the size of the PL collection region. Moreover, unlike the confocal microscope of Dixon et al., discussed herein above, the spectrally resolved components of the on-axis photoluminescence are not spectrally contaminated with off-axis photoluminescence of another wavelength because no monochromator or spectrometer is integrated directly within the detection arm of the optical system, as discussed herein above.

Figure 4:
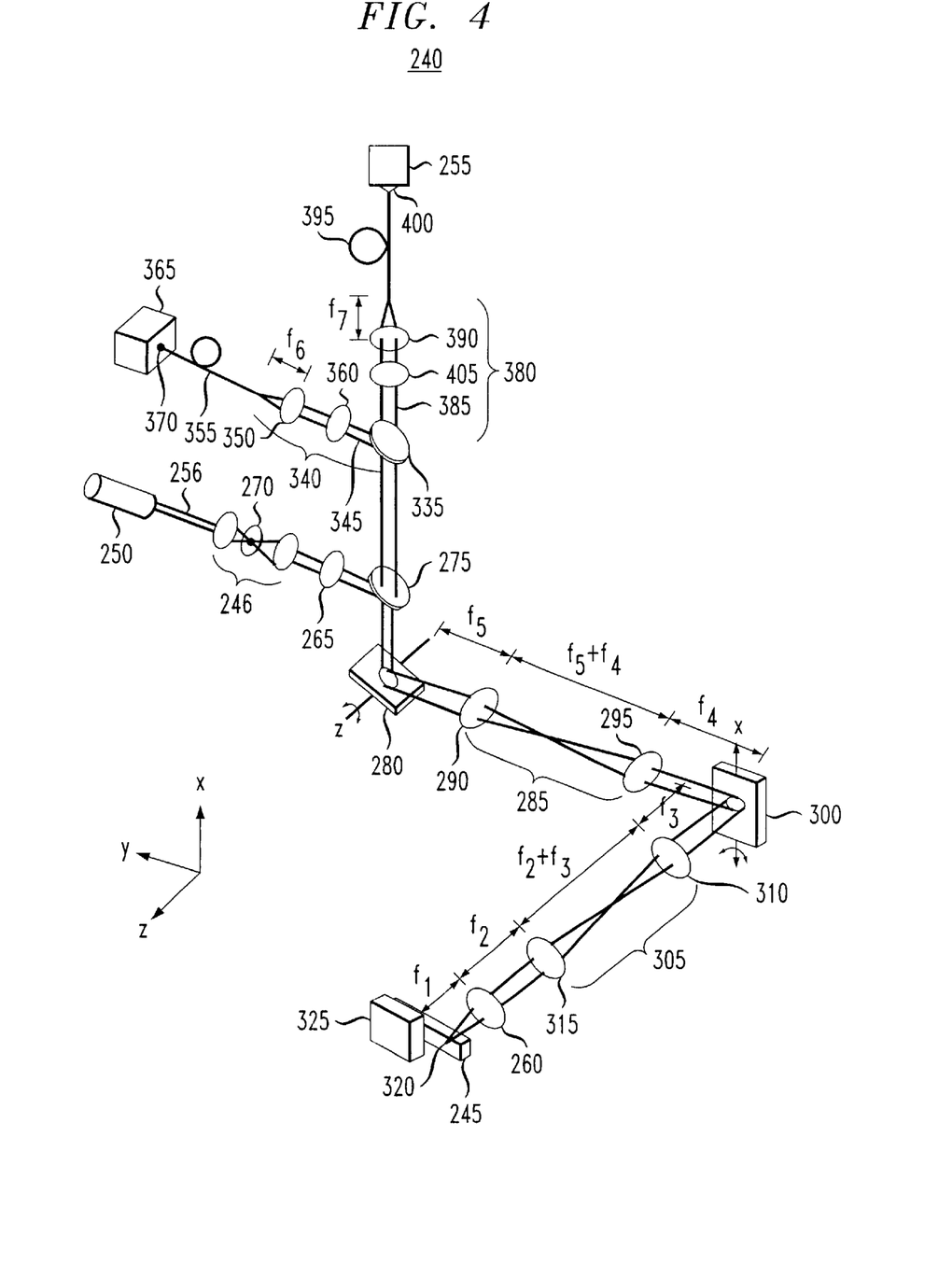
FIG. 4 is a perspective view of the optical system of the present invention.

Shown in FIG. 4 is optical system 240 in accordance with the principles of the invention for performing photoluminescence microscopy and/or spectroscopy on a semiconductor specimen 245, comprising a laser 250 and a photodetector 255. As is known in the art, optically induced emission from semiconductor specimen 245, known as "photoluminescence (PL)," may be used to provide information about the electronic and compositional properties of the semiconductor specimen. Using a beam expander 246, incoming coherent beam 256 from laser 250, operating at a wavelength $\lambda_1$, is expanded to fill the entrance aperture, $w_1$, of objective lens 260 (e.f.l.=$f_1$). This so-called "pumping beam" is used to photo-excite the specimen. Typically, lasing wavelengths having energies above the bandgap energy of the semiconductor specimen are used to photo-excite electron-hole pairs in the semiconductor specimen. In compound semiconductors, for example, such as GaAs and InP, a direct bandgap leads to radiative recombination of the electron-holes pairs. This radiative process or photoluminescence, however, is less efficient near defects that provide non-radiative recombination paths, allowing electrons to recombine without emitting a photon.

Preferably, a narrow bandpass filter 265 is employed to remove spectral components at wavelengths different than the lasing wavelength of laser 250. If desired, a spatial filter 270, such as a pinhole, may also be used within beam expander 246. Coherent light 256 is partially reflected by a beamsplitter 275 so as to strike a scanning mirror (X-scan) 280 that deflects the beam along the x-axis. An afocal telescope 285, preferably consisting of lens 290 (e.f.l.=$f_5$) and lens 295 (e.f.l.=$f_4$), maintains the incoming beam at the center of a second scanning mirror (Y-scan) 300, which deflects the beam along the y-axis. To do so, X scanning mirror 280 is positioned at the back focal point ($f_5$) of lens 290. A second afocal telescope 305, similarly consisting of lens 310 (e.f.l.=$f_3$) and lens 315 (e.f.l.=$f_2$), centers the incoming beam within the entrance pupil of objective lens 260, which then focuses the "pumping" beam to a diffraction limited spot 320 (~1–2 μm diameter) at the surface of, or inside, semiconductor specimen 245. To maintain centering, Y scanning mirror 300 is located at the back focal point ($f_3$) of lens 310, as well as at the focal point ($f_4$) of lens 295. Also, objective lens 260 is preferably positioned a distance $f_2$ away from lens 315.

Scanning mirrors 280 and 300 are computer controlled to deflect the beam so as to raster focused beam 320 on semiconductor specimen 245, and, preferably, at video rates so as to generate displays compatible with standard video monitors. Advantageously, the lifetime of the photoluminescence is sufficiently small to prevent pixel-to-pixel crosstalk at video scan rates. The position of the semiconductor specimen can be changed by moving translation stages 325 along the x and y axes.

Figure 5:
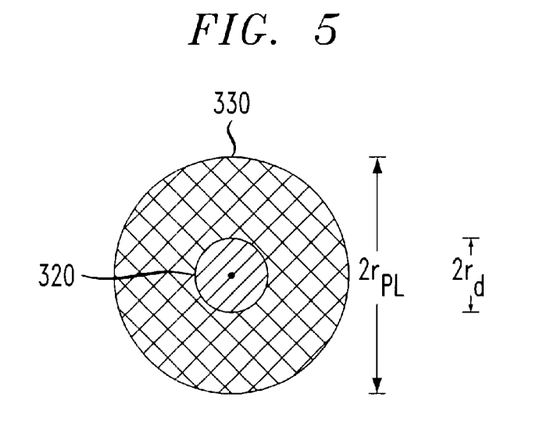
FIG. 5 is an enlarged top view of the diffraction limited focal spot and carrier diffusion spot of the optical system of FIG. 4.

As is well known in the art, the radius rd of the central portion of diffraction limited spot 320 is given by:

$$r_d = \frac{1.22\lambda_1}{2NA_{obj}} \quad (1)$$

where $NA_{obj}$ is the numerical aperture of objective lens 260. Note, however, that lateral carrier diffusion, particularly for non-defective regions, causes photoluminescence to occur beyond the radius of focal spot 320, shown in FIG. 5 as carrier diffusion spot 330 of radius $r_{p1}$ ($r_{p1}$>>$r_d$) Emitted photoluminescence from semiconductor specimen 245, including a portion from carrier diffusion spot 330, is collected by objective lens 260, passed back through the optical system, descanned by the scanning mirrors to form a fixed beam, and then partially reflected through beam splitter 335 into a spectroscopy detection arm 340 of the optical system. This latter beam 345 is focused by a detector lens 350 (e.f.l.=$f_6$) to the entrance aperture of optical fiber 355, either single-mode or multi-mode, which is positioned a distance $f_6$ in front of detector lens 350. Preferably, an optical filter 360, positioned between beam splitter 335 and optical fiber 355, transmits the band of wavelengths where the photoluminescence is expected, while blocking most of light at the lasing wavelength used to excite the semiconductor specimen.

Preferably, the entrance aperture of optical fiber 355 is confocal with focal spot 320 at the focal point of objective lens 260. Although the collected photoluminescence is from an area wider than focal spot 320, only the photoluminescence impinging on the surface, and within the numerical aperture of optical fiber 355 is coupled and detected, as more fully discussed herein below.

In accordance with the principles of the invention, the size of the region from which the photoluminescence is collected (the "PL collection region"), is primarily controlled by judiciously choosing the core radius and numerical aperture $NA_{fiber}$ of optical fiber 355 so as to limit the field of view. In other words, photoluminescence originating only from the desired PL collection region will be coupled into optical fiber 355. An optical spectrum analyzer 365 coupled to the opposing end 370 of optical fiber 355 is then used to resolve the individual spectral components of the collected photoluminescence.

Importantly, photoluminescence microscopy can also be performed, individually or in combination with spectroscopy, by also partially transmitting a portion of the collected photoluminescence into a microscopy detection arm 380 of the optical system. This latter transmitted beam 385 is focused by a second detector lens 390 (e.f.l.=$f_7$) onto a second optical fiber 395 positioned a distance $f_7$ in front of detector lens 390, making the entrance aperture similarly confocal with focal spot 320. Photodetector 255 is coupled to opposing end 400 of optical fiber 395. Likewise, an optical filter 405 positioned between beam splitter 335 and optical fiber 395 transmits the band of wavelengths where the photoluminescence is expected, while again blocking most of the light at the excitation wavelength. Similarly, although the collected photoluminescence is from an area wider than focal spot 320, only the photoluminescence impinging on the surface, and within the numerical aperture of optical fiber 395 is coupled and detected. The detector's signal is then digitized, stored in memory and displayed on a video monitor by a computer, thereby generating highly spatially resolved photoluminescence images. As noted aboveherein, focal spot 320 is raster at video rates so as to produce displays compatible with standard video monitors.

Figure 6:
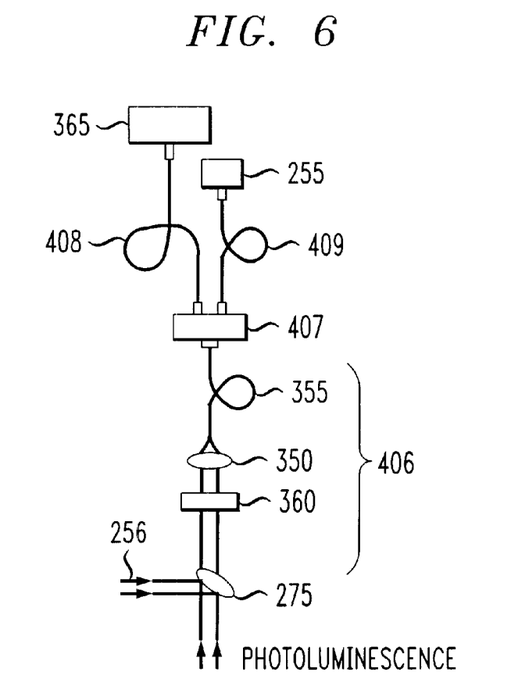
FIG. 6 is an alternative embodiment of the microscopy and spectroscopy arms of the optical system of the present invention.

Alternatively, the spectroscopy and microscopy detection arms can utilize the benefits of optical switches and splitters, thereby simplifying alignment, as further illustrated in FIG. 6. Similarly, emitted photoluminescence from semiconductor specimen 245 is collected by objective lens 260, passed back through the optical system and, and then transmitted through beam splitter 275 into a spectroscopy/microscopy detection arm 406 of the optical system. In this latter embodiment, the transmitted beam is likewise focused by detector lens 350 to the entrance aperture of optical fiber 355, with optical filter 360 transmitting the band of wavelengths where the photoluminescence is expected, while blocking most of light at the lasing wavelength used to excite semiconductor specimen 245. Optical fiber 355, however, is connected to an optical fiber switch 407 using standard ST, SC or FC connectors, which under program control directs the collected photoluminescence along either optical fiber 408 (spectroscopy detection arm) or optical fiber 409 (microscopy detection arm), each connected to an output port of the optical fiber switch. To perform spectroscopy, the collected photoluminescence is switched to optical fiber 408, thereby directing the photoluminescence to optical spectrum analyzer 365. When performing microscopy, the collected photoluminescence is instead switched along optical fiber 409 which, for example, is pigtailed to photodetector 255. It is contemplated that both spectroscopy and microscopy can be performed if optical fiber switch 407 is replaced with a passive optical fiber splitter, thereby splitting the collected photoluminescence along both optical fibers 408 and 409.

Optical spectral analyzers employing conventional free space gratings, such as a conventional monochromator, may be used to measure the spectra of the photoluminescence. In this case, light egressing from optical fiber 355 is typically coupled into the entrance slit of the monochromator and reflected off an internal diffraction grating at an angle proportional to the wavelength, thereby separating the photoluminescence into its spectral components along a longitudinal axis. The spectrum of the light may then be analyzed on the basis of the angle at which the light is diffracted by moving the diffracted light over a slit that is positioned in front of a detector. To optimally couple the light into the monochromator, however, the numerical aperture of opposing end 370 of optical fiber 355 is matched to the input numerical aperture of the entrance slit of the monochromator. Alternatively, opposing end 370 itself may be used as the entrance slit of the monochromator, simplifying alignment.

Of course, the grating monochromator may be replaced with spectrometers that employ wavelength tunable optical filters, such as a Fabry-Perot interferometer, to resolve the individual spectral components. Fabry-Perot interferometers consist of highly reflective, parallel mirrors that act as a resonant cavity, which transmits light only at a unique frequency (wavelength). Wavelength tuning is accomplished by varying the mirror spacing or by rotating the interferometer with respect to the incident light so as to provide a measure of the optical power as a function of wavelength.

Other OSAs known in the art may still further be used, such as those based on the Michelson interferometer, wherein the incident light is split into two paths. One path is fixed in length, and the other is variable so as to create an interference pattern between the signal and a delayed version of itself, known as an interferogram. The wavelength of the incident light can be determined by comparing the zero crossings in the interferogram with those for a known wavelength standard. The optical spectrum is determined by performing a Fourier transform on the interferogram.

In the above manner, the optical system of the present invention measures the intensity of the photoluminescence emitted from the semiconductor specimen as a function of position (x,y) and wavelength to perform both microscopy and/or spectroscopy. Note that spectroscopy can be performed on the specimen while the wavelength is scanned to record the full spectrum at a fixed position on the specimen, or at a fixed wavelength band while the focused beam is scanned across the semiconductor specimen, or a combination of both.

In accordance with the teachings of the present invention, it has been discovered that when the lateral carrier diffusion area exceeds the diffraction limit spot, an optical analysis that includes the extended size of the carrier diffusion area provides a technique for more properly controlling the size of the PL collection region or the axial photoluminescence resolution. The optical system is uniquely characterized in that the optical fiber(s) functions as the effective field stop for off-axis photoluminescence. As the field stop, the optical fiber(s) limits the size or field of view of the photoluminescence corresponding to the PL collection region. Importantly, it does so, however, by limiting the cone of light accepted from the off-axis photoluminescence vis-a-via its core size and numerical aperture.

Figure 7:
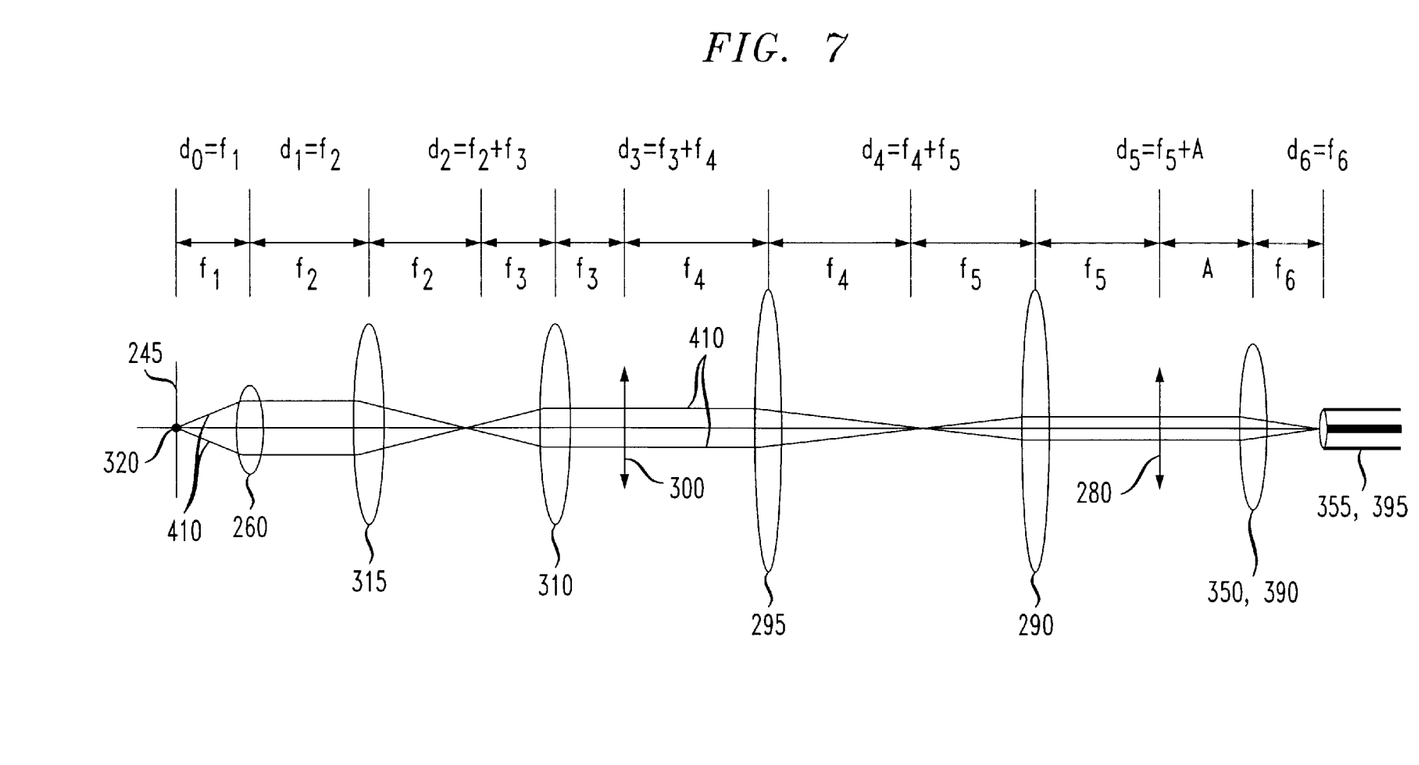
FIG. 7 is a schematic diagram of the optical system of FIG. 4, depicting the paths of the axial rays.

For the sake of simplicity, the optical system of FIG. 4 has been "unfolded," and labeled with the focal lengths ($f_n$) and spacings ($d_n$) of the lens elements, as depicted in FIG. 7. Inasmuch as the photoluminescence is passed back through the optical system and descanned, the orientation of the scanning mirrors is not relevant when unfolding the optical system of FIG. 4. By following the path of the axial rays of the photoluminescence (depicted herein as solid lines 410), it can be seen that objective lens 260 is the aperture stop of the optical system which limits the size of the axial cone of light from the photoluminescence region that reaches the optical fiber. All of the other lens elements and mirrors are large enough to accept a bigger cone. Optical fiber 355 has an "acceptance cone" or numerical aperture $NA_{fiber}$ large enough to accept a substantial portion of the axial cone of energy specified by the numerical aperture $NA_{obj}$ of objective lens 260.

Figure 8:
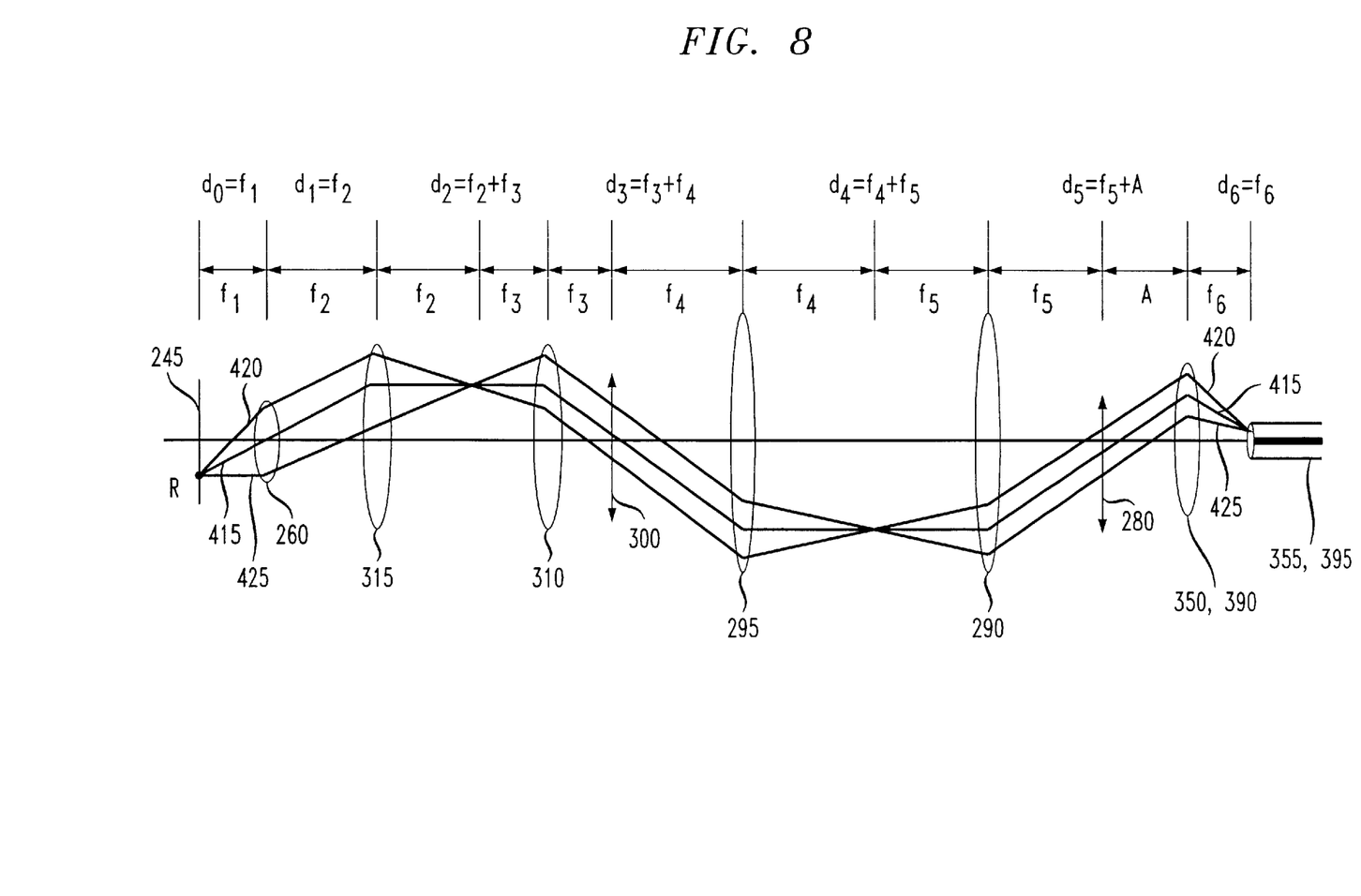
FIG. 8 is a schematic diagram of the optical system of FIG. 4 depicting the paths of the principal ray, and the lower and upper off-axis marginal rays.

Some distance off the optical axis, however, the situation is quite different. Referring now to FIG. 8, by following the. photoluminescence path of the principal ray (solid line 415) from an off-axis point R on specimen 245 as well as the rays through the upper and lower rims of the aperture stop (shown herein as solid lines 420 and 425, respectively), it can be seen that the photoluminescence is bound by the core size of the optical fiber. Specifically, the photoluminescence accepted from point R is limited by the periphery or the size of the core radius. This is more clearly depicted in FIG. 9, which is an enlarged section of optical fiber 355 receiving principal ray 415 as well as off-axis marginal rays 420 and 425. For some object point just further from the optical axis than off-axis point R, no rays at all enters the fiber, with the rays just missing the core. Enlarging the core diameter of the optical fiber, however, allows rays further from the axis to be coupled into the fiber, which in turns enlarges the field of view of the optical system.

Figure 9:
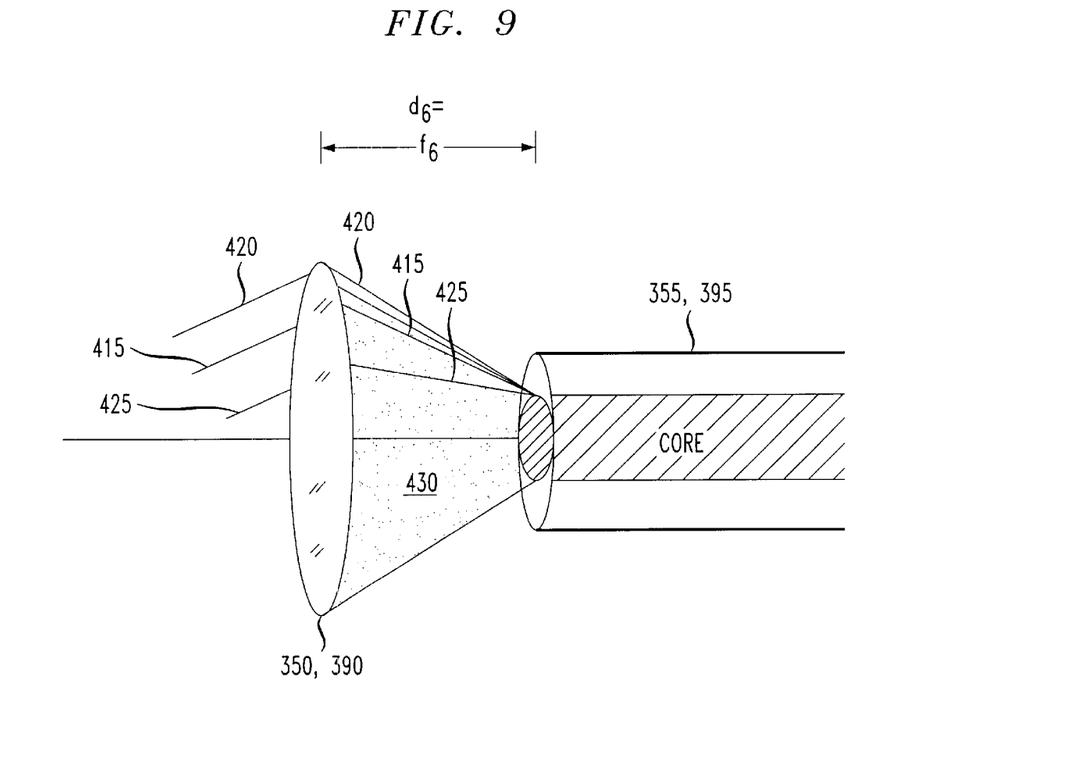
FIG. 9 is an enlarged side view of the fiber lens and optical fiber of FIG. 4, useful in illustrating how the optical fiber functions or acts as the field stop.

It should be understood that the cone of energy accepted from point R is also limited by the numerical aperture $NA_{fiber}$ (shown herein as stippled region 430) of the optical fiber. It should be understood that the cone of rays which lies within the acceptance cone of the fiber (i.e., having ray angles less than the numerical aperture of the fiber) becomes narrower as the photoluminescence point on the semiconductor specimen moves off-axis. Indeed, the cone of energy accepted from point R, in this case, is limited on its upper marginal ray 420 by the numerical aperture. The size of the accepted cone of light from point R is less than it would be if the numerical aperture was not a limiting factor. This effect is similar to "vignetting," and causes a reduction in the amount of photoluminescence collected at the conjugate image point on the optical fiber (referred herein as "numerical aperture vignetting") At some point still further from the axis than R, no light will be accepted by the optical fiber(s) since all rays incident on the core exceed the maximum external slope of the ray that can be totally internal reflected within the fiber. It can be seen that no light enters the fiber when the slope of its associated lower marginal ray 425 exceeds the numerical aperture of the fiber, and hence no photoluminescence is coupled into optical spectrum analyzer 365 or photodetector 255. This assumes, of course, that the core radius of the fiber is large enough for the incoming rays to hit the core. Otherwise, the rays similarly do not enter the optical fiber(s). As such, the field of view and, hence the PL collection region can be determined by judiciously choosing the numerical aperture and the core radius of the optical fiber(s).

Thus, the underlying rational in controlling the spatial resolution for an extended region of photoluminescence (the PL collection region) is to judiciously choose the core radius, and the numerical aperture of the optical fiber(s) so as to control the conical bundle of rays from the point on the periphery of the desired region of photoluminescence so as to reach and enter the optical fiber(s). Preferably, however, the core radius is used to control the size of the PL collection region to reduce the amount of numerical aperture vignetting, and maximize the coupling efficiency.

Using the above underlying rational, we can examine the relationship among the numerical aperture of the optical fiber, its core radius, and the size of the desired PL collection region by ray tracing through the optical system the principal and off-axis marginal rays from a point on the periphery of the PL collection region of radius $r_p$, which defines the desired field of view. This can be done by treating the optical system of FIG. 4 in terms of its component focal lengths and spacings, and then using the set of transfer equations below to determine the heights and slopes of the rays from lens element to lens element:

$$u'_n = u_n + y_n \phi_n \quad (2)$$

$$y_{n+1} = y_n - d u'_n \quad (3)$$

where $y_n$ is the height of the ray from the optical axis at the $n^{th}$ element, $u_n$ and $u'_n$ are the slope of the ray before and after refraction through the nth element, respectively, $\phi_n$ is the optical power of the $n^{th}$ element, and $d_n$ is the distance between the $n^{th}$ and $n^{th}+1$ elements. For a detailed discussion on the use of transfer equations to perform ray tracing, see, for example, Chapter 2 of the book entitled *Modern Optical Engineering*, Warren J. Smith, McGraw-Hill Book Company (1966).

Note that because principal ray 415 passes through the center of the aperture stop, we insert a ray height of $y_{p1}=0$ at objective lens 260, giving an initial ray slope $u_0=-r_p/f_1$. The off-axis marginal rays 420, 425, however, pass through the upper and lower rims of objective lens 260 at respective ray heights of $y_1=-f_1 NA_{obj}$ and $y_u=f_1 NA_{obj}$, giving initial ray slopes of $u_{u0}=NA_{obj}-r_p/f_1$ and $u_{10}=-NA_{obj}-r_p/f_1$, respectively, recalling that $NA_{obj}$ is the numerical aperture of objective lens 260. The tabulation of the raytrace data is shown below in Table 1, wherein $m_1=f_2/f_3$ and $m_2=f_4/f_5$ are the magnifications of afocal telescopes 305 and 285, respectively. The raytrace data for principal ray 415 is shown in lines 3 and 4 ($y_p$, $u_p$), whereas the data for off-axis marginal rays 420 and 425, are shown in lines 7 and 8 ($y_u$, $u_u$), and lines 5 and 6 ($Y_L$, $U_L$), respectively. The total magnification of the telescopes, $m_3$, is given by $m_3=m_1 m_2$. Note that the distance between X scanning mirror 280 and lens 350 has been denoted by A, and is sufficiently large to accommodate the optics necessary to introduce incoming beam 256 into the optical system.

Without any loss of generality or applicability for the principles of the invention, the raytrace data below is preformed with respect to optical fiber 355. It should be clearly understood that the analysis is substantially the same for optical fiber 395 used for performing microscopy, except that lens 350 is replaced with lens 390, and A is now the distance between X scanning mirror 280 and lens 390.

TABLE 1

| | PL area 330 (n = 0) | lens 260 (n = 1) | lens 315 (n = 2) | lens 310 (n = 3) | lens 295 (n = 4) | lens 290 (n = 5) | lens 350 (n = 6) | fiber 355 (n = 7) |
|---|---|---|---|---|---|---|---|---|
| 1 $\phi$ | | $1/f_1$ | $1/f_2$ | $1/f_3$ | $1/f_4$ | $1/f_5$ | $1/f_6$ | |
| 2 d | $d_0 = f_1$ | $d_1 = f_2$ | $d_2 = f_2 + f_3$ | $d_3 = f_3 + f_4$ | $d_4 = f_4 + f_5$ | $d_5 = f_5 + A$ | $d_6 = f_6$ | |
| 3 $y_p$ | $-r_p$ | 0 | $\dfrac{r_p f_2}{f_1}$ | $\dfrac{r_p f_2}{f_1}$ | $\dfrac{-m_1 f_4 r_p}{f_1}$ | $\dfrac{f_4 m_1 r_p}{f_1}$ | $\dfrac{m_3 A r_p}{f_1}$ | $\dfrac{m_3 r_p f_6}{f_1}$ |
| 4 $u_p$ | | $-\dfrac{r_p}{f_1}$ | $-\dfrac{r_p}{f_1}$ | 0 | $\dfrac{r_p m_1}{f_1}$ | 0 | $-\dfrac{r_p m_3}{f_1}$ | $\dfrac{r_p m_3 \left(\dfrac{A}{f_6}-1\right)}{f_1}$ |
| 5 $y_L$ | $-r_p$ | $-f_1 NA_{obj}$ | $-f_1 NA_{obj} + \dfrac{r_p f_2}{f_1}$ | $\dfrac{f_1 NA_{obj}}{m_1} + \dfrac{r_p f_2}{f_1}$ | $\dfrac{f_1 NA_{obj}}{m_1} - \dfrac{r_p m_1 f_4}{f_1}$ | $\dfrac{-f_1 NA_{obj}}{m_3} - \dfrac{r_p m_1 f_4}{f_1}$ | $\dfrac{-f_1 NA_{obj}}{m_3} + \dfrac{A r_p m_3}{f_1}$ | $\dfrac{r_p f_6 m_3}{f_1}$ |
| 6 $u_L$ | | $NA_{obj} - \dfrac{r_p}{f_1}$ | $\dfrac{-r_p}{f_1}$ | $\dfrac{-NA_{obj} f_1}{f_2}$ | $\dfrac{r_p m_1}{f_1}$ | $\dfrac{f_1 NA_{obj}}{m_1 f_4}$ | $-\dfrac{r_p m_3}{f_1}$ | $\dfrac{-NA_{obj} f_1}{f_6 m_3} + \dfrac{r_p m_3 (A-f_6)}{f_1 f_6}$ |
| 7 $y_U$ | $-r_p$ | $f_1 NA_{obj}$ | $f_1 NA_{obj} + \dfrac{r_p f_2}{f_1}$ | $\dfrac{-f_1 NA_{obj}}{m_1} + \dfrac{r_p f_2}{f_1}$ | $\dfrac{-f_1 NA_{obj}}{m_1} - \dfrac{r_p m_1 f_4}{f_1}$ | $\dfrac{f_1 NA_{obj}}{m_3} - \dfrac{r_p m_1 f_4}{f_1}$ | $\dfrac{f_1 NA_{obj}}{m_3} + \dfrac{A r_p m_3}{f_1}$ | $\dfrac{r_p f_6 m_3}{f_1}$ |

TABLE 1-continued

| | PL area 330 (n = 0) | lens 260 (n = 1) | lens 315 (n = 2) | lens 310 (n = 3) | lens 295 (n = 4) | lens 290 (n = 5) | lens 350 (n = 6) | fiber 355 (n = 7) |
|---|---|---|---|---|---|---|---|---|
| 8 $u_U$ | | $-NA_{obj} - \dfrac{r_p}{f_1} \dfrac{-r_p}{f_1}$ | | $\dfrac{NA_{obj}f_1}{f_2}$ | $\dfrac{r_p m_1}{f_1}$ | $\dfrac{-f_1 NA_{obj}}{m_1 f_4}$ | $-\dfrac{r_p m_3}{f_1}$ | $\dfrac{NA_{obj}f_1}{f_6 m_3} + \dfrac{r_p m_3 (A - f_6)}{f_1 f_6}$ |

It is noteworthy that the above raytrace data is only valid if objective lens 260 is actually the aperture stop. In practice, this can be accomplished by performing a ray trace analysis which also includes the clear aperture (CA) of each lens and the ratio of the clear aperture (CA) to the height (y) that the axial ray strikes the element (CA/y). Objective lens 260 is assured to be the aperture stop if the element for which this ratio is the smallest is objective lens 260. Otherwise, other element or elements in the optical system will, in an unexpected manner, limit the conical bundle of light reaching the optical fiber. Also, recall that the this analysis is only valid if the PL collection region is substantially larger than the diffraction pattern of focal spot 320.

Since photoluminescence incident outside the core of optical fiber 355 is not detected, limiting the PL collection region to a radius $r_p$ requires that the ray height of principal ray 415 matches the core radius of the fiber, $r_c$. Photoluminescence from any point outside this radius will have its conjugate image outside the radius of the core. Setting the ray height of the principal ray at the fiber ($Y_{p7}$) (line 3 of the raytrace data) to the core radius, $r_c$, yields:

$$r_c = y_{p7} = \frac{r_p m_3 f_6}{f_1} \quad (4)$$

and, then solving for $r_p$, we obtain, $$r_p = \frac{f_1 r_c}{m_3 f_6} \quad (5)$$

Of course, the above constraint requires that at least some of photoluminescence falls within the acceptance cone or numerical aperture of the optical fiber, so as not to be the limiting factor. This requires that the some of the ray angles of the photoluminescence hitting the core of fiber (bounded by the angles of the off-axis marginal ray, $u'_{U6}$ and $u'_{L6}$), lie within the numerical aperture $NA_{fiber}$ of the optical fiber. Of course, if the signs of the ray angles of the off-axis marginal rays are not equal, then a portion of photoluminescence will always lie within the numerical aperture of the optical fiber since there is at least one ray angle of zero. Otherwise, if $u'_{L6}$ and $u'_{U6}$ have the same sign, the numerical aperture $NA_{fiber}$ of the optical fiber 355 should at least be a numerical aperture $NA_{min}$ that is greater than the absolute value of the minimum ray angle of the off-axis marginal rays, $u'_{L6}$, $u'_{U6}$. This latter numerical aperture constraint can be expressed mathematically as follows:

$$NA_{fiber} > NA_{min} = |u'_{L6}| \text{ if } |u'_{L6}| < |u'_{U6}| \quad (6)$$

or $$NA_{fiber} > NA_{min} = |u'_{U6}| \text{ if } |u'_{U6}| < |u'_{L6}| \quad (7)$$

We can get the slopes $u'_{L6}$, $u'_{U6}$ of the off-axis marginal rays 420, 425 incident on the fiber from lines 6 and 8 of the raytrace data. Inserting the expression for $r_p$ from Eq. (5) into the expression for the slopes, then transforms Eqs. (6) and (7) into the following:

$$NA_{fiber} > NA_{min} = |u'_{L6}| = \left| -\frac{NA_1 f_1}{f_6 m_3} + \frac{(A - f_6) r_c}{f_6^2} \right|, \text{ if } |u'_{L6}| < |u'_{U6}| \text{ or} \quad (8)$$

$$NA_{fiber} > NA_{min} u'_{U6} = \left| \frac{NA_1 f_1}{f_6 m_3} + \frac{(A - f_6) r_c}{f_6^2} \right|, \text{ if } |u'_{U6}| < |u'_{L6}| \quad (9)$$

If $A >> f_6$, which is typically the case, then we can replace $(A - f_6)$ with A, to obtain the following:

$$NA_{fiber} > NA_{min} = |u'_{L6}| = \left| -\frac{NA_1 f_1}{f_6 m_3} + \frac{A r_c}{f_6^2} \right|, \text{ if } |u'_{L6}| < |u'_{U6}| \quad (10)$$

$$NA_{fiber} > NA_{min} = |u'_{U6}| = \left| \frac{NA_1 f_1}{f_6 m_3} + \frac{A r_c}{f_6^2} \right|, \text{ if } |u'_{U6}| < |u'_{L6}| \quad (11)$$

Accordingly, the size of the region from which the photoluminescence is collected (the PL collection region) can be controlled by judiciously choosing the core diameter and numerical aperture ($NA_{fiber}$) of the optical fiber in accordance with Eqs.(5), (10)and (11). If the desired radius of the PL collection region, however, cannot be achieved using standard core radii and numerical apertures known in the art, then various optical parameters can, of course, be modified, particularly, the numerical aperture $NA_{obj}$, and focal lengths $f_1$, $f_6$ of lenses 260, and 350.

Alternatively, the numerical aperture of the optical fiber can be tailored to be the limiting factor in controlling the radius $r_p$ of the PL collection region, instead of the core radius. Recall that at some off-axis point, no light will be accepted by the optical fiber since all rays incident on the core exceed the maximum external slope of the ray that can be totally internal reflected within the fiber. Contrastingly, in this later case, the minimum ray angle of the off-axis marginal rays (in this case marginal ray 425) from the periphery of the desired PL collection region $r_p$ should just match the numerical aperture $NA_{fiber}$ of the optical fiber:

$$NA_{fiber} = |u'_{L6}| \text{ if } |u'_{L6}| < u'_{U6}| \quad (12)$$

$$NA_{fiber} = |u'_{U6}| \text{ if } |u'_{U6}| < u'_{L6}| \quad (13)$$

Obtaining the expressions for the slopes of the off-axis marginal rays from the raytrace data, we can solve $r_p$ in terms of $NA_{fiber}$, as follows:

$$|r_p| = \left| \frac{f_1 f_6}{A m_3} \left( NA_{fiber} + \frac{f_1 NA_{obj}}{f_6 m_3} \right) \right| \text{ if } |u'_{L6}| < |u'_{U6}| \text{ or} \quad (14)$$

$$|r_p| = \left| \frac{f_1 f_6}{A m_3} \left( NA_{fiber} - \frac{f_1 NA_{obj}}{f_6 m_3} \right) \right| \text{ if } |u'_{U6}| < |u'_{L6}| \quad (15)$$

In the above latter case, however, all the photoluminescence from the periphery of the desired radius $r_p$ should reach a conjugate image inside the core, thus requiring the core radius to have a minimum radius $r_{min}$ equal to the absolute value of the principal ray height $y_{p7}$ at the fiber. Obtaining the ray height $y_{p7}$ from the raytrace data, we can express this condition as follows:

$$|r_{min}| = \left| r_p \frac{f_6}{f_1} m_3 \right| \quad (16)$$

where $r_p$ is the value obtained from Eqs. (14) and (15).

Accordingly, the size of the PL collection region can also be controlled by judiciously choosing the core diameter and numerical aperture $NA_{fiber}$ of the optical fiber in accordance with Eqs. (14)–(16). Again, if the desired radius of the PL collection region cannot be achieved using standard core radii and numerical apertures, then various optical parameters can, of course, be modified.

It is noteworthy that when the focal length of lens 350 increasingly becomes larger than that of lens 260, it is easier to control the region of the PL collection region through the core radius of the optical fiber, instead of the numerical aperture, and vice-a-versus. This can be better understood by noting that the ray angles of the off-axis marginal rays become steepest as the focal length of lens 350 decreases, as expected, and for points farther from the axis are less likely to lie within the numerical aperture of the optical fiber.

The above developed optical analysis, made on the basis of geometrical considerations of the PL collection region, thus establishes the parameters of the optical fiber(s) required to control the size of the PL collection region, which size is dependent on pump power density and resolution, and material considerations. It is contemplated, however, that the optical system of the present invention can be used to measure key properties of semiconductor materials and devices, particularly those where the expected photoluminescence lies near or about either the 1300 or 1500 nm lightwave communication bands.

For illustration purposes, and to gain a better understanding of the present invention, exemplary calculations can be made for a preferred embodiment with the elements of the optical system as follows, and with respect to optical fiber 355:

lever arm: A=450 mm;
lens 260: effective focal length, f1=7.8 mm, numerical aperture, $NA_{obj}$=0.6;
lens 315: effective focal length, f2=0 mm;
lens 310: effective focal length, f3=25 mm;
lens 295: effective focal length f4=75 mm;
lens 290: effective focal length, f5=40 mm;
lens 350: effective focal length, f6=8 mm;

Table II below shows the relationship between radius $r_p$ of the PL collection region for different core radii and numerical apertures, where the core size is desired to be the limiting factor in controlling the radius of the PL collection region.

TABLE II

| Fiber Type | Fiber Parameters | PL collection Region radius, $r_p$ Eq. (5) | $u'_{L6} \leftrightarrow u'_{U6}$ Eqs. (10) (11) | $NA_{min}$ Eqs. (10) (11) |
|---|---|---|---|---|
| Multimode | $r_c$ = 31.25 μm, $NA_{fiber}$ = 0.21 | 10.2 μm | .02 ↔ .41 | 0.02 |
| Multimode | $r_c$ = 25 μm, $NA_{fiber}$ = 0.21 | 8.1 μm | −0.02 ↔ .37 | Not applicable |
| Single-Mode | $r_c$ = 4.5 μm $NA_{fiber}$ = 0.1 | 1.5 μm | −0.16 ↔ 0.23 | Not applicable |

Note in the first example that the core limit applies ($NA_{fiber} > NA_{min}$), whereas in the last two examples, the ray angles of the off-axis marginal rays are of unequal signs, thus ensuring that at least a portion of the photoluminescence enters the core of the optical fiber. Note, however, that diffraction effects can enlarge the size of the PL collection region, particularly where the desired PL collection region approaches the size of the diffraction pattern of focal spot 320.

Table III below likewise shows the relationship between the core radius of the optical fiber, and its numerical aperture, but where the limiting factor should be the numerical aperture $NA_{fiber}$. To better illustrate this point, we have, however, replaced lens 350 with a 4 mm lens.

TABLE III

| Fiber Type | Fiber Parameters | PL collection Region radius, $r_p$ Eqs. (14) (15) | $r_{min}$ Eq. (16) |
|---|---|---|---|
| Multimode | $r_c$ = 31.25 μm $NA_{fiber}$ = 0.21 | 13.8 μm | 21.2 μm |
| Multimode | $r_c$ = 25 μm, $NA_{fiber}$ = 0.21 | 13.8 μm | 21.2 μm |
| Single-Mode | $r_c$ = 4.5 μm $NA_{fiber}$ = 0.1 | 11.3 μm | 17.3 μm |

Note in the first two examples that the NA limit applies ($r_c > r_{min}$), whereas in the last example, the optical fiber does not, however, have the required minimum core radius. In such a case, the radius of the PL collection region is determined instead by the size of the core radius. Using Eq.(5), the radius of the PL collection region is calculated to be instead about 2.9 μm, but will have a weak or low photoluminescence collection efficiency.

Of course, similar calculations can be made with respect to optical fiber 395 used to perform photoluminescence microscopy.

Although the parameters of the optical fiber(s) can be specifically tailored to the desired radius of the PL collection region, which is based on lateral carrier diffusion and power density considerations, it may be preferable to have an inventory of optical fibers having a range of different core radii and numerical apertures. Then, based on design considerations, one can be chosen from inventory with the closet desired core radius and numerical aperture. In general, increasing the number of optical fibers kept affords greater design control, but there will usually be a benefit/cost tradeoff.

One primary advantage of the present invention is that it can readily utilize fiber technology to enhance performance. For example, optical amplifiers can be built into the optical fiber(s) to increase the signal level of the collected photoluminescence, without the need to increase the power level of the light used to excite the semiconductor specimen.

For example, portions or all of optical fibers 355, 395 can be replaced with fiber based amplifier(s), chosen to have an optical gain spectrum that substantially matches the band of wavelengths where the photoluminescence is expected. Such fiber based amplifiers may include the use of Erbium doped as well as Praseodymium and Neodymium doped fibers, among other rare earth doped elements, wherein counterpropagating or bidirectional pumping is used to effect amplification. It such cases, however, it is expected that a spectral calibration will be required due to the non-uniformity in the spectral gain curve of the optical amplifiers.

Figure 10:
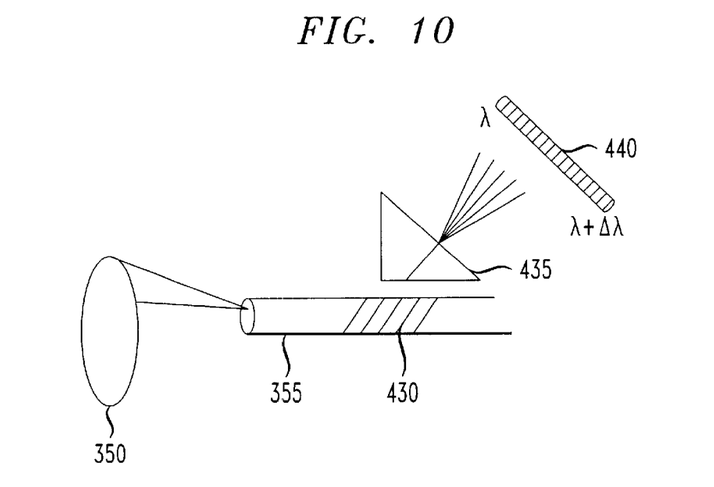
FIG. 10 is a simplified schematic diagram of an optical spectrum analyzer (OSA) employing a fiber bragg grating.

Additionally, the ready utilization of fiber technology allows a spectrometer to be,built within optical fiber 355, allowing a more efficient light path for spectrally resolving the photoluminescence, as well as resulting in a more compact system. In this latter case, fiber based spectrum analyzers which employ fiber bragg gratings may be used to measure the optical spectrum. More particularly, a fiber bragg grating 430 consisting of a periodic variation in the refractive index of the fiber's core can be fabricated in optical fiber 355, which variation will be denoted by heavy marks. See, for example, Lightwave Applications of Fibre Bragg Gratings, *IEEE Journal of Lightwave Technology*, Vol. 15, No. 8, August 1997, pp. 1391–1404. In this latter case, the incident photoluminescence is reflected off diffraction grating 430 and coupled outside at an angle proportional to the wavelength through the use of an external prism 435, as shown in FIG. 10. The spectrum of the light is then analyzed on the basis of the angle at which the light is diffracted using a detector array 440, in a manner known in the art. Preferably, however, the all fiber based optical spectrum analyzer disclosed in co-inventor's pending application Ser. No. 09/338,226 entitled "Optical Spectrum Analyzer" is preferred, which application is incorporated herein by reference. Of course, other optical spectrum analyzers (OSAs) known in the art can also be used.

It should be understood that the embodiments herein above are merely illustrative of the principles of the invention. Various modifications may be made by those skilled in the art which will embody the principles of the invention and fall within the spirit and the scope thereof.

What is claimed is:

1. An optical system for performing photoluminescence microscopy and/or spectroscopy on a semiconductor specimen, comprising:
   an illumination source for producing an illumination beam propagating along an optical path towards the semiconductor specimen;
   means for focusing said illumination beam to a diffraction limited spot on or within said semiconductor specimen so as to optically induce photoluminescence from said semiconductor specimen; and
   means for detecting the photoluminescence emitted from the photoluminescence region, including
      an optical fiber having first and second opposing ends, said first opposing end receiving the photoluminescence collected from the semiconductor specimen, wherein said first opposing end functions as the field stop for off-axis photoluminescence so as to limit the photoluminescence to a collection region on the semiconductor region of a predetermined radius larger than that of the diffraction limited spot.

2. The optical system of claim 1 further comprising means for scanning the diffraction limited spot in a predetermined pattern on said semiconductor specimen.

3. The optical system of claim 1 wherein the entrance aperture of said optical fiber is confocal with the diffraction limited spot.

4. The optical system of claim 1 wherein the radius of the collection region is determined by the numerical aperture and the core radius of the said optical fiber.

5. The optical system of claim 4 wherein the numerical aperture of said optical fiber is the limiting factor in determining the size of the collection region.

6. The optical system of claim 4 wherein the core radius of said optical fiber is the limiting factor in determining the size of the collection region.

7. The optical system of claim 1 wherein said optical fiber includes a fiber based optical amplifier.

8. The optical system of claim 1 wherein said optical fiber includes a fiber bragg grating.

9. The optical system of claim 1 wherein said optical fiber includes an all fiber based optical spectrum analyzer.

10. The optical system of claim 1 further comprising an optical spectrum analyzer coupled to the second opposing end of said optical fiber.

11. The optical system of claim 10 wherein said optical spectrum analyzer is a grating monochromator, and the numerical aperture of the second opposing end of the optical fiber substantially matches the input numerical aperture of the grating monochromator.

12. The optical system of claim 11 wherein the second opposing end of the optical fiber acts like an entrance slit for the grating monochromator.

13. The optical system of claim 1 further comprising an optical detector coupled to the second opposing end of said optical fiber.

14. An optical system for performing photoluminescence microscopy and spectroscopy on a semiconductor specimen, comprising:
   an illumination source for producing an illumination beam propagating along an optical path towards the semiconductor specimen;
   means for focusing said illumination beam to a diffraction limited spot on or within said semiconductor specimen so as to optically induce photoluminescence from said semiconductor specimen;
   means for scanning the diffraction limited spot in a predetermined pattern on said semiconductor specimen;
   a microscopy detection arm receiving photoluminescence from said semiconductor specimen comprising a photodetector and a first optical fiber directing collected photoluminescence to said photodetector, whereby the first optical fiber acts like a field stop for off-axis photoluminescence so as to limit the collected photoluminescence to a collection region on the semiconductor specimen of a predetermined radius larger than that of the diffraction limited spot; and
   a spectroscopy detection arm also receiving photoluminescence from said semiconductor specimen comprising an optical spectrum analyzer and a second optical fiber directing collected photoluminescence to said optical spectrum analyzer, whereby the second optical fiber likewise acts like a field stop for limiting the collected photoluminescence to the collection region.

15. The optical system of claim 14 further comprising an optical fiber switch and a third optical fiber directing collected photoluminescence from the semiconductor specimen to said optical fiber switch, and said optical fiber switch switching collected photoluminescence between said spectroscopy and said microscopy arm.

16. The optical system of claim 14 further comprising an optical fiber splitter and a third optical fiber directing collected photoluminescence from the semiconductor specimen to said optical fiber splitter, and said optical fiber splitter splitting collected photoluminescence along said spectroscopy and said microscopy arms.

17. The optical system of claim 14 wherein the entrance aperture of said first optical fiber is confocal with the diffraction limited spot.

18. The optical system of claim 14 wherein the entrance aperture of said second optical fiber is confocal with the diffraction limited spot.

19. The optical system of claim 14 wherein the radius of the collection region is determined by the numerical apertures and the core radii of the said first and second optical fibers.

20. The optical system of claim 19 wherein the numerical apertures of said first and second optical fibers are the limiting factors in determining the size of the collection region.

21. The optical system of claim 19 wherein the core radii of said first and second optical fibers are the limiting factors in determining the size of the collection region.

22. The optical system of claim 14 wherein said first and second optical fibers include fiber based optical amplifiers.

23. The optical system of claim 14 wherein said optical spectrum analyzer is an all fiber based optical spectrum analyzer.

24. The optical system of claim 14 wherein said optical spectrum analyzer is a grating monochromator, and the input numerical aperture of said first optical fiber substantially matches the input numerical aperture of the grating monochromator.

25. An optical system for performing photoluminescence microscopy and/or spectroscopy on a semiconductor specimen, comprising:

an illumination source;

means for focusing said illumination beam to a diffraction limited spot on or within said semiconductor specimen so as to optically induce photoluminescence from said semiconductor specimen;

means for scanning the diffraction limited spot in a predetermined pattern on said semiconductor specimen; and means for detecting the photoluminescence emitted from a desired collection region on the semiconductor specimen of a predetermined radius $r_p$, including an optical fiber having first and second opposing ends, said first opposing end receiving the collected photoluminescence, wherein the optical fiber has a core size such that off-axis photoluminescence from the periphery of said desired collection region has a conjugate image within the radius of the core of said optical fiber, and wherein the optical fiber has a numerical aperture sufficiently large to accept at least a portion of off-axis photoluminescence from the periphery of the desired collection region.

26. The optical system of claim 25 wherein the entrance aperture of said optical fiber is confocal with the diffraction limited spot.

27. The optical system of claim 25 wherein said optical fiber includes a fiber based optical amplifier.

28. The optical system of claim 25 wherein said optical fiber includes a fiber bragg grating.

29. The optical system of claim 25 wherein said optical fiber includes an all fiber based optical spectrum analyzer.

30. The optical system of claim 25 further comprising an optical spectrum analyzer coupled to the second opposing end of said optical fiber.

31. The optical system of claim 30 wherein said optical spectrum analyzer is a grating monochromator, and the numerical aperture of the second opposing end of the optical fiber substantially matches the input numerical aperture of the grating monochromator.

32. The optical system of claim 31 wherein the second opposing end of the optical fiber acts like an entrance slit of the grating monochromator.

33. The optical system of claim 25 further comprising an optical detector coupled to the second opposing end of said optical fiber.

34. An optical system for performing photoluminescence microscopy and/or spectroscopy on a semiconductor specimen, comprising:

an illumination source;

means for focusing said illumination beam to a diffraction limited spot on or within said semiconductor specimen so as to optically induce photoluminescence from said semiconductor specimen;

means for scanning the diffraction limited spot in a predetermined pattern on said semiconductor specimen; and means for detecting the photoluminescence emitted from a desired collection region on the semiconductor specimen of a predetermined radius $r_p$, including an optical fiber having first and second opposing ends, said first opposing end receiving collected photoluminescence wherein the optical fiber has a numerical aperture substantially equal to the absolute value of the minimum ray angel of the off-axis marginal rays from the periphery of the desired collection region, and wherein the optical fiber has a core size sufficiently large that off-axis photoluminescence from the periphery of said desired collection region has a conjugate image within the radius of the core of the optical fiber.

35. The optical system of claim 34 wherein the entrance aperture of said optical fiber is confocal with the diffraction limited spot.

36. The optical system of claim 34 wherein said optical fiber includes a fiber based optical amplifier.

37. The optical system of claim 34 wherein said optical fiber includes a fiber bragg grating.

38. The optical system of claim 34 wherein said optical fiber includes an all fiber based optical spectrum analyzer.

39. The optical system of claim 34 further comprising an optical spectrum analyzer coupled to the second opposing end of said optical fiber.

40. The optical system of claim 34 wherein said optical spectrum analyzer is a grating monochromator, and the numerical aperture of the second opposing end of the optical fiber substantially matches the input numerical aperture of the grating monochromator.

41. The optical system of claim 40 wherein the second opposing end of the optical fiber acts like an entrance slit of the grating monochromator.

42. The optical system of claim 34 further comprising an optical detector coupled to the second opposing end of said optical fiber.

* * * * *